United States Patent [19]

Vry et al.

[11] Patent Number: 5,702,350
[45] Date of Patent: Dec. 30, 1997

[54] ADAPTER FOR CONNECTING A STEREOSCOPIC ENDOSCOPE TO ELECTRONIC DOCUMENTATION DEVICES

[75] Inventors: Uwe Vry, Aalen; Ottmar Sager, Heidenheim; Fritz Strähle, Heubach-Lautern; Martin Poxleitner, Königsbronn, all of Germany

[73] Assignee: Carl-Zeiss-Stiftung, Heidenheim, Germany

[21] Appl. No.: 531,333

[22] Filed: Sep. 20, 1995

Related U.S. Application Data

[63] Continuation of Ser. No. 184,678, Jan. 21, 1994, abandoned, which is a continuation-in-part of Ser. No. 100,276, Aug. 2, 1993, abandoned.

[30] Foreign Application Priority Data

| Aug. 1, 1992 | [DE] | Germany | 42 25 507.4 |
| Jan. 21, 1993 | [DE] | Germany | 43 01 466.6 |
| Jun. 9, 1993 | [DE] | Germany | 9308618 U |

[51] Int. Cl.$^6$ ............................................. A61B 1/00
[52] U.S. Cl. ............................................. 600/166
[58] Field of Search ............................ 600/101, 102, 600/112, 136, 111, 166; 359/462, 466, 376–378; 348/45, 75

[56] References Cited

U.S. PATENT DOCUMENTS

| 3,486,806 | 12/1969 | Werner . |
| 4,061,135 | 12/1977 | Widran et al. . |
| 4,149,769 | 4/1979 | Zobel . |
| 4,364,629 | 12/1982 | Lang et al. . |
| 4,436,369 | 3/1984 | Bukowski . |
| 4,518,231 | 5/1985 | Muchel et al. . |
| 4,571,038 | 2/1986 | Jako . |
| 4,601,550 | 7/1986 | Yoshino et al. . |
| 4,651,201 | 3/1987 | Schoolman . |
| 4,834,518 | 5/1989 | Barber . |
| 4,836,188 | 6/1989 | Berry . |
| 4,905,082 | 2/1990 | Nishigaki et al. . |
| 4,964,710 | 10/1990 | Leiner . |
| 5,122,650 | 6/1992 | McKinley . |
| 5,192,969 | 3/1993 | Igarashi et al. ............. 355/22 |
| 5,205,280 | 4/1993 | Dennison, Jr. et al. . |
| 5,282,085 | 1/1994 | Volkert et al. . |
| 5,295,477 | 3/1994 | Janfaza . |
| 5,321,447 | 6/1994 | Sander et al. . |

FOREIGN PATENT DOCUMENTS

| 0019792 | 12/1980 | European Pat. Off. . |
| 1996605 | 11/1968 | Germany . |
| 1766803 | 9/1971 | Germany . |
| 289924 | 5/1991 | Germany . |
| 4116810 | 11/1992 | Germany . |
| 9300529 | 5/1993 | Germany . |

*Primary Examiner*—Richard J. Apley
*Assistant Examiner*—John Leubecker
*Attorney, Agent, or Firm*—Walter Ottesen

[57] ABSTRACT

An adapter is provided for connecting a stereoscopic endoscope having intertwined stereo beam paths to electronic documentation devices. The adapter has a releasable connection to the endoscope at a location at which the stereoscopic component images are not yet completely separated. A second releasable connection between the first releasable connection and the end of the adapter can be provided which faces toward the electronic documentation devices in order to provide a variable adaptation to different optics diameters of the stereoscopic endoscope.

13 Claims, 4 Drawing Sheets

ADAPTER FOR CONNECTING A STEREOSCOPIC ENDOSCOPE TO ELECTRONIC DOCUMENTATION DEVICES

RELATED APPLICATIONS

This is a continuation of application Ser. No. 08/184,678, filed on Jan. 21, 1994, (abandoned) which is a continuation-in-part of application Ser. No. 08/100,276, filed on Aug. 2, 1993, (abandoned).

FIELD OF THE INVENTION

The invention is directed to an adapter for connecting electronic documentation devices to a stereoscopic endoscope.

BACKGROUND OF THE INVENTION

U.S. Pat. No. 5,612,816 is incorporated herein by reference and discloses a stereoscopic endoscope which has a small optics diameter and, at the same time, guarantees a good stereo impression. The stereoscopic endoscope has intertwined stereo beam paths; that is, the stereo beam paths run in a single tube-shaped housing and are transmitted via a common optical system. The intermediate images generated by the stereoscopic endoscope are viewed directly by means of optical viewing devices or are recorded by electronic documentation devices. For the purpose of direct viewing it is, for example, possible to mount the stereoscopic endoscope via a connection piece on a surgical microscope. As an alternative to this configuration, it is also, for example, possible to mount downstream of the endoscope CCD-receivers or CCD-cameras as electronic documentation devices for recording the stereoscopic component images.

If the arrangement described in the above-mentioned patent application is now used strictly as a TV endoscope (that is, in combination with electronic documentation devices), then a series of requirements is imposed on an apparatus combination of this kind in an operating room.

First, a simple sterilization, such as autoclaving, of the endoscope should be possible. For this purpose, the electronic documentation devices must be removed from the endoscope.

In addition, the electronic documentation devices and, if required, various stereoscopic endoscope optics with, for example, different optical diameters, should be exchangeable without difficulty. A substantial compatibility of individual components is here especially required; that is, the same adapter having integrated electronic documentation devices should be useable in combination with different endoscope optics.

German utility model registration G 93 00 529.6, for example, discloses mounting an adapter on a stereoscopic endoscope having completely separate stereo beam paths. The adapter is suitable for receiving two cameras. Here, the interface between the endoscope and the adapter must guarantee a highly precise adjustment of these parts to each other. Because of the separate stereo beam paths of the endoscope, a complex adjustment precisely to the optical axes of the two stereoscopic viewing beam paths is required in order to avoid possible binocular errors or rotations when there is a defective relative orientation.

SUMMARY OF THE INVENTION

It is therefore an object of the invention to provide an adapter for connecting electronic documentation devices to a stereoscopic endoscope wherein the stereoscopic beam paths are transmitted via a common optical system. Here, it is necessary to provide a simple sterilization in addition to an easy exchangeability of the stereoscopic endoscope and the electronic documentation devices.

The adapter of the invention is for connecting electronic documentation devices to a stereoscopic endoscope having a common optical system for transmitting unseparated stereo beam paths. The adapter includes releasable connecting means for connecting the adapter to the endoscope at a location where the stereo beam paths remain unseparated.

When changing the endoscopic optics in the operating zoom, no critical adjusting problems of any kind occur because the invention provides a releasable connection between the adapter and the stereoscopic endoscope at a location where the stereoscopic beam paths are not yet completely separate. In the adapter, the two stereo beam paths are fixedly adjusted to each other because the stereo beam paths pass through a common optic. Here, it is noted that, in principle, no adjustment is necessary in the endoscope tube.

The sterilization problem is now solved in a simple manner with the aid of the adapter of the invention because, after separating endoscope and adapter, the endoscope is autoclaved in a manner known per se or is immersed in a disinfecting bath. The adapter, on the other hand, can be provided with a conventional cover or likewise be immersed in a suitable disinfecting bath.

A further advantageous embodiment of the adapter of the invention provides for a two-part adapter configuration having a second releasable connection in the adapter. This second releasable connection then defines a second interface which is between the first releasable connection and the end of the adapter which faces toward the electronic documentation devices. An optical system is mounted in the part of the adapter which faces toward the electronic documentation devices. This optical system adapts the various realizable stereo bases of the endoscope optics to a defined fixed stereo basis of the electronic documentation devices. Here, it is possible to provide exchangeable adapter parts for different optics diameters of the stereoscopic endoscope so that, for different optics diameters, only a single adapter part having fixed integrated electronic documentation devices is required.

In addition to the embodiment described, various releasable connections such as engaging or threaded connections are suitable as releasable connections.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
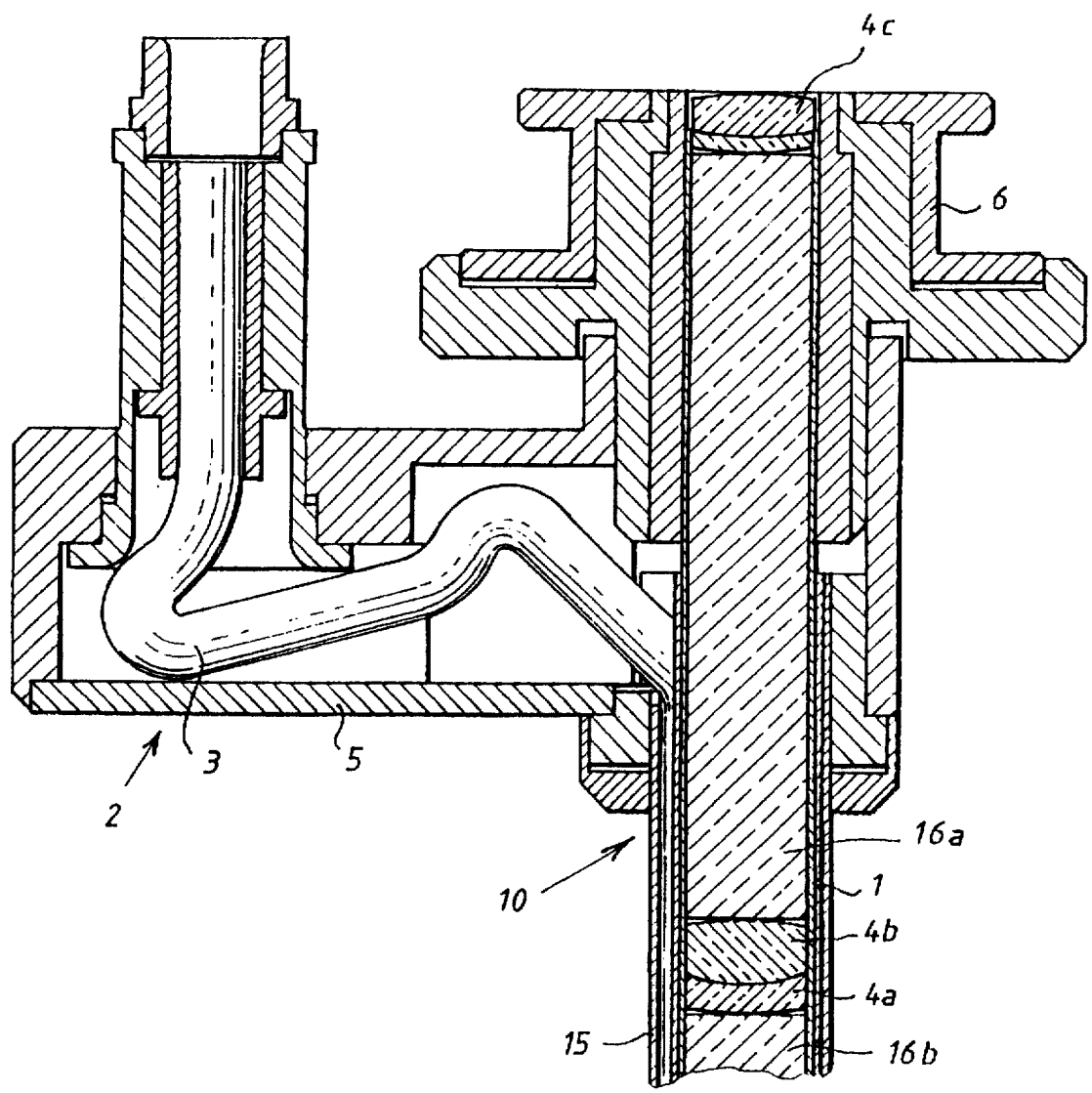
FIG. 1 is a side elevation view, in section, of the proximal part of the stereoscopic endoscope which is releasably connected to a first embodiment of the adapter of the invention.

In FIG. 1, only the upper part of the stereoscopic endoscope 10 is shown which is connected to a first embodiment of the adapter of the invention. A series of optical elements (4a, 4b, 4c) is mounted in the endoscope housing 1 as disclosed in the above-mentioned U.S. Pat. No. 5,612,816, which is incorporated herein by reference.

The corresponding dimensions of the optical elements (4a, 4b, 4c) ensure that the stereoscopic endoscope 10 has a single beam path comprising two intertwined stereo beam paths and that the stereoscopic endoscope supplies an intermediate image at the viewing end which is either viewed directly or, however, can be recorded by electronic documentation devices. As mentioned above, it is understood in the following, that intertwined stereo beam paths are those stereo beam paths which are transmitted by a common optical system.

The last intermediate image, which is supplied by the optical system of the stereoscopic endoscope 10, is positioned in the endoscope 10 within a region which is delimited by the last optical element 4c and the next-to-last element 4b of the endoscope at the viewing end, preferably in the plane of the next-to-last optical element 4b of the endoscope 10. The last optical element 4c at the viewing end serves as an objective which images the intermediate image at infinity, that is, the endoscope 10 has a parallel beam path at the output end. In the embodiment shown, glass rods (16a, 16b) are mounted between the individual optical elements (4a, 4b, 4c) of the stereoscopic endoscope 10. These glass rods are, however, not absolutely necessary for the function of the stereoscopic endoscope including the adapter of the invention.

The stereoscopic endoscope furthermore includes an illuminating device 2 which is attached laterally to the housing 1 of the optical system. The illuminating device comprises essentially a further housing 5 in which a light conductor 3 or a suitable light-conducting guide is mounted. In the embodiment shown, the housing 5 of the illuminating device 2 is cemented to the housing 1 of the optical system. Alternatively this connection can also be configured as being releasable in the form of a threaded connection.

Light of an externally mounted radiation source (not shown) is coupled into the light conductor 3. A xenon lamp serves, for example, as a radiation source. The light conductor is guided on the endoscope housing 1 in the direction of the object detail to be viewed. In addition to the actual endoscope housing 1, a further external endoscope housing 15 is provided wherein the light conductor 3 is guided in the direction toward the viewing location.

The part of the releasable connection facing toward the endoscope is mounted above the housing 5 of the illuminating device 2. This part is configured as a bayonet insert 6 of a bayonet connection which, in the embodiment shown, operates as a releasable engaging connection. An engaging connection having a dove-tail guide can be used as an alternative to the engaging connection configured as a bayonet connection. Furthermore, it is possible to configure the releasable connection as a threaded connection with the particular thread or the threaded insert mounted in dependence upon the configuration at the endoscope or at the adapter. The stereoscopic endoscope is connected in each embodiment releasably to the adapter via the selected connection with the electronic documentation devices being mounted in the adapter. The stereoscopic endoscope and the adapter can at any time be quickly separated from each other and again be reconnected.

Figure 2A:
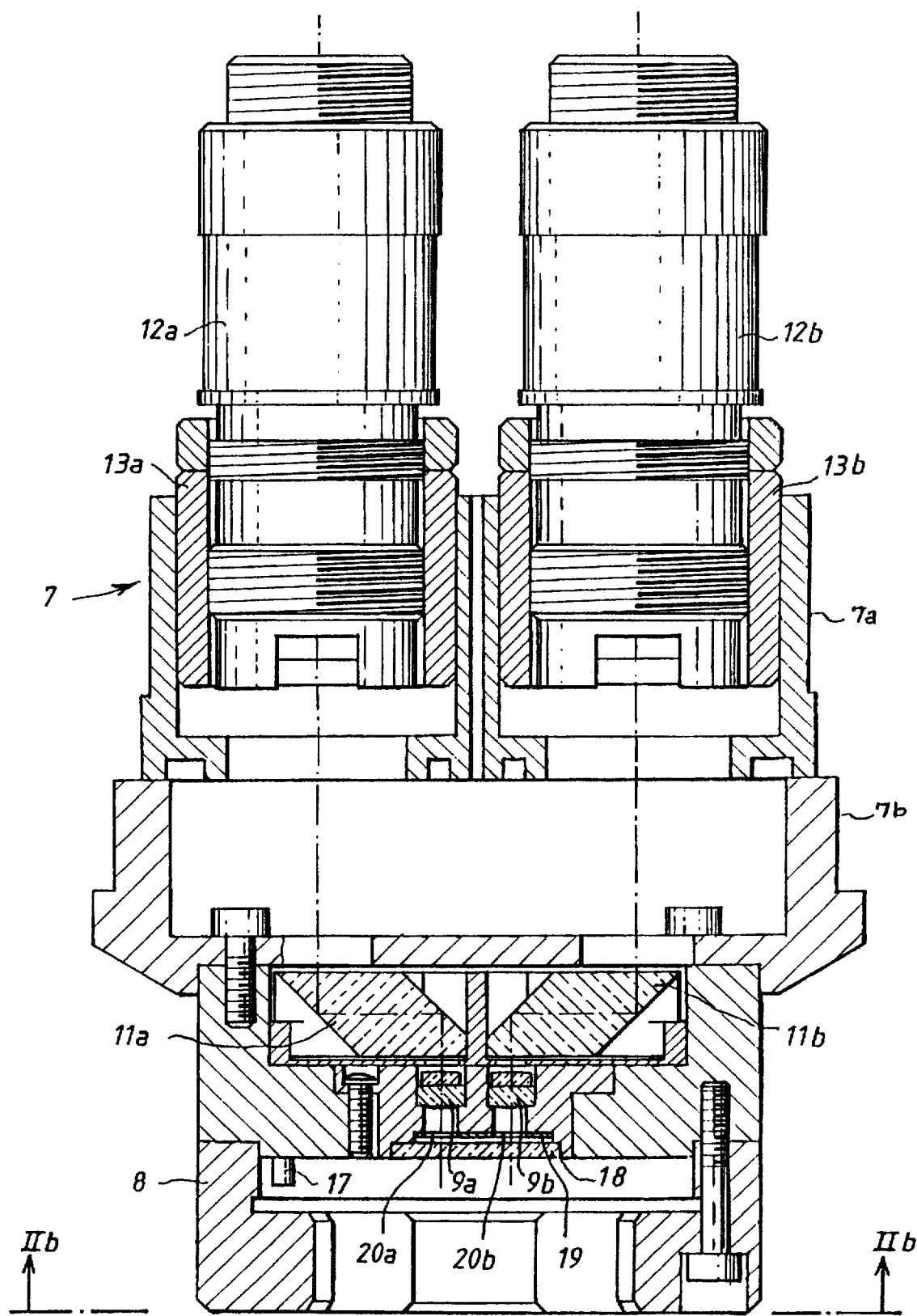
FIG. 2a is a front view, in section, through the first embodiment of the adapter of the invention.

In FIG. 2a, an embodiment of the adapter 7 of the invention is shown in a front view, that is, a corresponding section of the adapter 7. The adapter 7 has the adapter-end counter piece for the bayonet connection of the stereoscopic endoscope at the entry end, that is, the bayonet receptacle 8.

As an alternative to the embodiment shown, the parts of the bayonet connection can be mounted in reverse on the adapter 7 and the endoscope 10, that is, the bayonet receptacle can be mounted on the endoscope and the bayonet insert on the adapter.

The interface between the adapter 7 and the endoscope, more specifically, the correspondingly configured releasable connection is, according to the invention, at a location where the intertwined stereo beam paths of the endoscope do not yet run completely separate from each other. A parallel beam path is present at this location. The final separation of the two stereo beam paths only takes place in the adapter according to the invention.

Complex adjusting work for the two downstream mounted electronic documentation devices becomes unnecessary because of the arrangement of the releasable connection at this location when there is a rapid exchange of adapter 7 and endoscope. This is so because the mountings of the adapter and endoscope must be adjusted precisely to the optical elements of the adapter 7 only when the adapter is assembled.

In the adapter 7 of the invention, the releasable connection, that is, the bayonet receptacle 8, is mounted upstream of a transparent plate 18, for example, of glass, which serves to seal off the adapter 7. A diaphragm 19 having two diaphragm apertures (20a, 20b), which are preferably of circular shape, is mounted adjacent to transparent plate 18 at the side thereof toward the viewing end. The diaphragm apertures determine the apertures of the two stereo beam paths. The two stereo beam paths are only at this location in the beam path completely separated by the diaphragm apertures (20a, 20b). Two component objectives (9a, 9b) as well as deflecting elements (11a, 11b) in the form of rhombic reflection prisms are mounted downstream of the two diaphragm apertures (20a, 20b). The deflecting elements (11a, 11b) function to correspondingly deflect the stereo beam paths in the direction of the electronic documentation devices (12a, 12b). In lieu of the deflection prisms used, it is also possible to use deflection mirrors as deflecting elements. Likewise, and as required, more than one deflecting element per stereo beam path can be mounted in the adapter 7 of the invention or, it can even be provided that one stereo beam path impinges without deflection upon an electronic documentation device while the other stereo beam path is deflected via a deflecting element.

In the embodiment shown, two CCD-cameras are releasably mounted in the adapter 7 as electronic documentation devices (12a, 12b) which receive the stereoscopic component images. In the embodiment shown, the CCD-cameras are threadably engaged in the corresponding threaded inserts (13a, 13b) in the adapter 7. The threaded inserts (13a, 13b) function as holders for the electronic documentation devices (12a, 12b). In this way, it is possible to provide focusing for the two CCD-cameras which are focused on different object planes in dependence upon the depth to which they are threadably engaged.

With the adapter assembly, it should be guaranteed that the threaded inserts (13a, 13b) of the adapter 7 as well as the optical elements in the adapter 7 such as component objectives (9a, 9b), deflecting elements (11a, 11b) and diaphragm 19 are adjusted precisely to each other. No critical adjustment problems occur when changing adapter 7 and the endoscope with the aid of the adapter of the invention.

The electronic documentation devices (12a, 12b) can also be displaced transversely to the stereo beam paths in order to provide a precise adjustment of these devices to the stereo beam paths. This is realized in the embodiment shown in that the adapter part 7a having the threaded inserts (13a, 13b) is movable within specific tolerances relative to the rest of the adapter 7 and therefore to the stereo beam paths. These specific tolerances are provided by the play between screws and their respective bores (not shown) which coact to hold adapter parts 7a and 7b together.

It is also possible to provide the upper part having the electronic documentation devices with a cover housing (not shown) which protects the electronic documentation devices against external influences such as dirt and the like.

Likewise not shown in FIG. 2a, are the required signal lines via which the recording signals of the electronic documentation devices (12a, 12b) are transmitted further. The signals supplied by the electronic documentation devices can, for example, be processed in an arrangement for displaying three-dimensional images in accordance with U.S. patent application Ser. No. 07/961,353, filed Oct. 15, 1992 now abandoned, and incorporated herein by reference, and can be sequentially shown on a display with a viewer wearing the correspondingly switched shutter spectacles. A combination of this kind is preferably used for minimally invasive surgery.

Figure 2B:
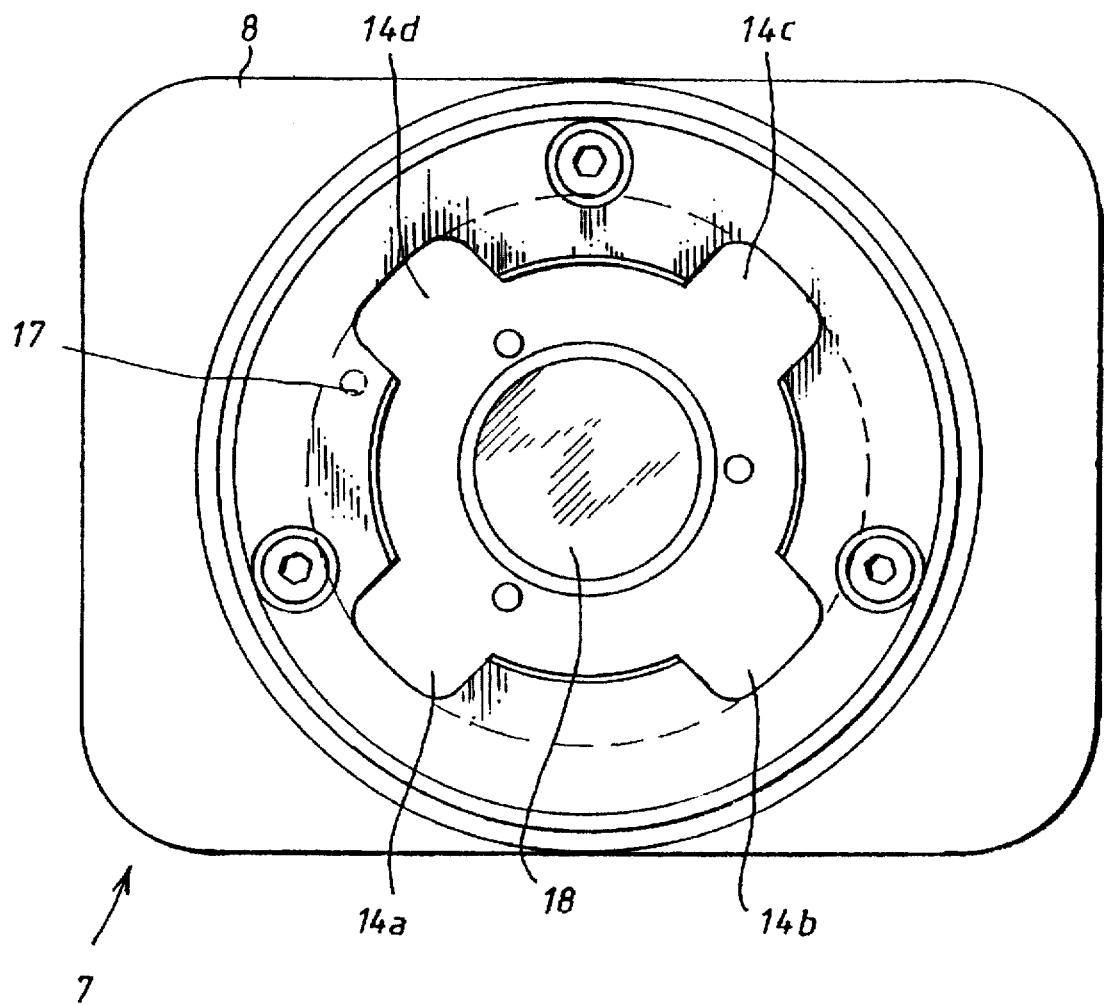
FIG. 2b is a view taken along line IIb—IIb of FIG. 2a and shows the releasable connection between the adapter and endoscope; and, FIG. 3 is a second embodiment of the adapter of the invention with a two-part assembly and a second releasable connection.

A view of the bayonet receptacle along line IIb—IIb of FIG. 2a is shown in FIG. 2b. The bayonet receptacle is for the releasable connection between adapter and endoscope. The bayonet counter piece on the endoscope engages in the cutouts (14a, 14b, 14c, 14d) of the bayonet receptacle 8 in the adapter of the invention and, after rotatation, latches in a defined position. The bayonet receptacle 8 includes a fixing pin 17 as a fixing element to ensure locking the connection in a precise position. The fixing element latches into a corresponding opposite cutout in the bayonet counter piece of the endoscope. One or more such fixing elements are advantageously provided also for an alternate threaded connection between adapter and endoscope.

Figure 3:
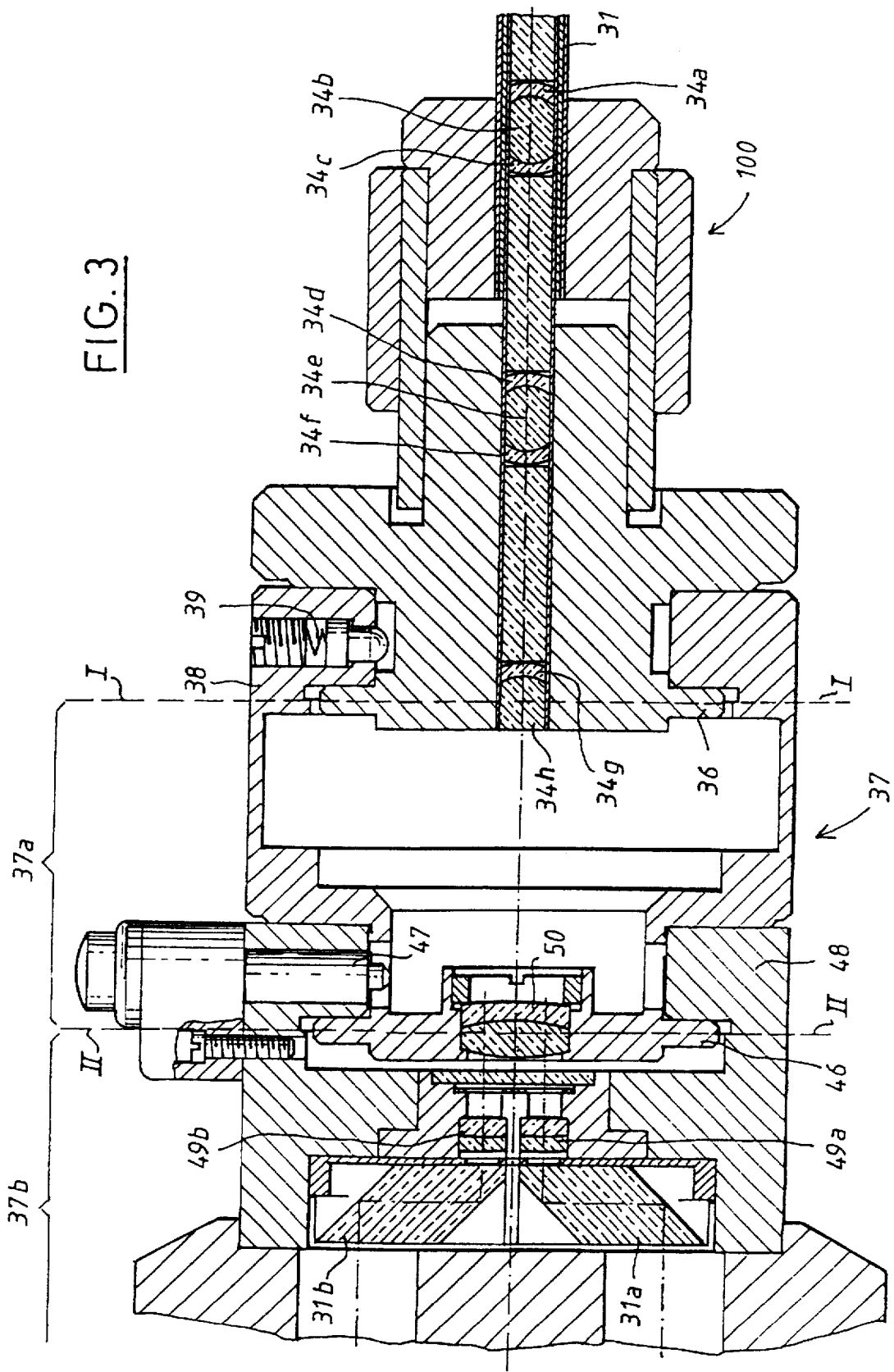

A second embodiment of the adapter 37 of the invention including a forward mounted stereoscopic endoscope 100 is shown in FIG. 3. The endoscope 100 used has basically the identical configuration of the endoscope of the first embodiment. Accordingly, a series of optical elements (34a to 34h) are arranged in an endoscope housing 31 and are dimensioned in correspondence to the first embodiment so that the two stereoscopic beam paths are transmitted via a common optical system. The optics diameter in the endoscope 100 is, however, selected smaller compared to the first embodiment which is necessary for specific applications, for example, in the ear-nose-throat area.

An intermediate image results at the viewing end which is recorded by the electronic documentation devices (not shown). As in the first embodiment, the stereoscopic endoscope 100 is mounted to the adapter 37 via a releasable connection. A bayonet connection again serves as a releasable connection and includes a bayonet insert 36 mounted on the endoscope 100 and the bayonet receptacle 38 on the adapter. Also, a fixing element 39 in the form of a resiliently biased pin is provided which guarantees a reproducible and reliable arrangement of the endoscope 100 on the adapter 37. All variations delineated in the first embodiment can be used as a releasable connection. This releasable connection is a first releasable connection and defines a first interface I.

The adapter 37 has a second releasable connection between the first releasable connection and the end of the adapter where the electronic documentation devices are mounted whereby a second interface II is defined in the adapter. This releasable connection is also configured as an engaging connection and is in the form of a bayonet connection with a bayonet receptacle 48 and a bayonet insert 46. Likewise, a fixing element 47 is provided so that a position-precise and reproducible arrangement is provided. Alternative embodiments are also possible for this releasable connection.

The second interface II in the adapter ensures that the complex adapter part 37b can be used with the two CCD-cameras as electronic documentation devices and forward mounted deflection prisms (31a, 31b) and component objectives (49a, 49b) for different optics diameters of the endoscope 100.

With the first interface I to the endoscope 100 in the other adapter part 37a, the adaptation of the different stereo bases of the various insertable endoscopes to the stereo basis of the CCD-cameras is provided with the aid of an optical system 50 mounted in the first adapter part. The stereo basis of the CCD-cameras is defined by the spacing of the two component objectives (49a, 49b) in the other adapter part 37b. In this way, it is ensured that the same adapter part 37b can always be used with the electronic documentation devices fixedly mounted therein notwithstanding endoscope optics diameters. Only the adapter part 37a having the first interface I and the suitable optical system 50 must be exchanged in dependence upon the particular optics diameter and this is possible without difficulty because of the releasable connections or interfaces provided.

It is understood that the foregoing description is that of the preferred embodiments of the invention and that various changes and modifications may be made thereto without departing from the spirit and scope of the invention as defined in the appended claims.

What is claimed is:

1. A stereoscopic endoscope for transmitting an intermediate image of an object, the stereoscopic endoscope comprising:

two electronic documentation devices for receiving said intermediate image;

a stereoscopic endoscope optical system defining an optical axis;

said stereoscopic endoscope optical system including common optical stereoscopic means mounted along and on said axis for transmitting unseparated intertwined stereo beam paths from the object in the direction of said axis and for providing said intermediate image;

said stereoscopic endoscope optical system further including an objective downstream of said common optical stereoscopic means for imaging said intermediate image at infinity along said unseparated intertwined stereo beam paths;

said objective having a clear diameter;

an adapter for connecting said stereoscopic endoscopic optical system to said electronic documentation devices;

said adapter having a first end facing toward said objective and a second end facing toward said electronic documentation devices;

said adapter including optical separating means between said first and second ends for completely separating said intertwined stereo beam paths from each other within said adapter and for transmitting the separated stereo beam paths to respective ones of said electronic documentation devices;

a releasable connector for connecting said first end of said adapter to said stereoscopic endoscope optical system at a location along said optical axis in front of said optical separating means where said stereo beam paths entering said adapter are and remain intertwined and unseparated;

said optical separating means being mounted in a fixed geometrical relationship with respect to said electronic documentation devices within said adapter;

two component objectives arranged in corresponding ones of said two beam paths downstream of said optical separating means when viewed in the direction of said beam paths from the object;

said two component objectives defining respective optical axes separated from each other by a spacing greater than said clear diameter; and, at least one deflecting element disposed in one of said beam paths downstream of the corresponding component objective so as to permit the light transmitted along said beam paths to impinge upon said documentation devices.

2. The stereoscopic endoscope of claim 1, said optical separating means comprising a diaphragm having two diaphragm apertures for completely separating the two beam paths from each other to provide two mutually separated beam paths.

3. The stereoscopic endoscope of claim 1, said adapter further comprising first and second holders releasably holding said documentation devices, respectively; and, adjusting means for adjusting said documentation devices in the direction of said beam paths.

4. The stereoscopic endoscope of claim 3, said two documentation devices being two CCD-cameras and said adjusting means being defined by thread means formed in said holders for threadably engaging the CCD-camera corresponding thereto for adjusting said documentation devices in the direction of said beam paths and for facilitating the insertion and removal thereof from the holder, respectively.

5. The stereoscopic endoscope of claim 1, comprising two of said deflecting elements disposed in corresponding ones of said beam paths so as to permit the light transmitted along said beam paths to impinge upon said documentation devices, respectively; and, said deflecting elements being respective deflecting prisms.

6. The stereoscopic endoscope of claim 1, said releasable connector being an insert engaging connection.

7. The stereoscopic endoscope of claim 6, said insert engaging connection being a bayonet connection.

8. The stereoscopic endoscope of claim 1, said releasable connector including fixing means for precisely fixing said releasable connector with respect to position.

9. A stereoscopic endoscope for transmitting an intermediate image of an object, the stereoscopic endoscope comprising:

two electronic documentation devices for receiving said intermediate image;

a stereoscopic endoscope optical system defining an optical axis;

said stereoscopic endoscope optical system including common optical stereoscopic means mounted along and on said axis for transmitting unseparated intertwined stereo beam paths from the object in the direction of said axis and for providing said intermediate image;

said stereoscopic endoscope optical system further including an objective downstream of said common optical stereoscopic means for imaging said intermediate image at infinity along said unseparated intertwined stereo beam paths;

said objective having a clear diameter;

an adapter for connecting said stereoscopic endoscopic optical system to said electronic documentation devices;

said adapter having a first end facing toward said objective and a second end facing toward said electronic documentation devices;

said adapter including twin aperture diaphragm means disposed between said first and second ends for completely separating said intertwined stereo beam paths from each other within said adapter and for transmitting the separated stereo beam paths to respective ones of said electronic documentation devices;

releasable connecting means for connecting said first end of said adapter to said stereoscopic endoscope optical system at a location along said optical axis upstream of said twin aperture diaphragm means where said stereo beam paths remain intertwined and unseparated;

said adapter further including two component objectives mounted downstream of said diaphragm means for focusing said beam paths onto said electronic documentation devices, respectively;

said two component objectives being arranged in corresponding ones of said two beam paths downstream of said diaphragm apertures, respectively, when viewed in the direction of said beam paths away from the object;

said two component objectives defining respective optical axes separated from each other by a spacing greater than said clear diameter; and, at least one deflecting element disposed in one of said beam paths downstream of the corresponding component objective so as to permit the light transmitted along said beam paths to impinge upon said documentation devices.

10. The stereoscopic endoscope of claim 9, said connecting means having a first connecting part mounted on said stereoscopic endoscope optical system and a second connecting part mounted on said first end of said adapter; and, said adapter further comprising a transparent plate mounted between said diaphragm means and said second connecting part.

11. The stereoscopic endoscope of claim 9, comprising two of said deflecting elements disposed in corresponding ones of said beam paths so as to permit the light transmitted along said beam paths to impinge upon said documentation devices, respectively; and, said deflecting elements being respective deflecting prisms.

12. The stereoscopic endoscope of claim 11, said releasable connecting means comprising a first connecting part mounted on said stereoscopic endoscope optical system and a second connecting part mounted on said first end of said adapter; and, said adapter further comprising a transparent plate mounted between said twin aperture diaphragm means and said second connecting part.

13. A stereoscopic endoscope for transmitting an intermediate image of an object to two electronic documentation devices, the stereoscopic endoscope comprising:

a stereoscopic endoscope optical system having a diameter and defining an optical axis;

said stereoscopic endoscope optical system including common optical stereoscopic means mounted along and on said axis for transmitting unseparated intertwined stereo beam paths from the object in the direction of said axis and for providing said intermediate image of the object;

an adapter for connecting said stereoscopic endoscopic optical system to the electronic documentation devices;

said adapter including a first part defining a first end of said adapter facing toward said stereoscopic endoscope optical system and a second part for holding said electronic documentation devices;

said second part defining a second end of said adapter facing away from said first end;

said adapter including twin aperture diaphragm means mounted in said second part between said first and second ends for completely separating said intertwined stereo beam paths from each other within said adapter and for transmitting the separated stereo beam paths to respective ones of said electronic documentation devices;

a first releasable connector for connecting said first part of said adapter to said stereoscopic endoscope optical system at a location along said optical axis upstream of said twin aperture diaphragm means where said stereo beam paths are and remain intertwined and unseparated;

said adapter further including component objectives mounted in said second part downstream of said diaphragm means for focusing said beam paths onto said electronic documentation devices, respectively;

said component objectives having a stereo basis defined by the spacing therebetween;

said first part having an objective mounted therein for imaging said intermediate image at infinity along said unseparated stereo beam paths and for optically adapting said stereo basis of said component objectives to said diameter of said stereoscopic endoscope optical system; and, a second releasable connector for connecting said first and second parts to each other.

\* \* \* \* \*

UNITED STATES PATENT AND TRADEMARK OFFICE
CERTIFICATE OF CORRECTION

PATENT NO. : 5,702,350
DATED : December 30, 1997
INVENTOR(S) : Uwe Vry, Ottmar Sager, Fritz Straehle and Martin Poxleitner It is certified that error appears in the above-identified patent and that said Letters Patent is hereby corrected as shown below:

```
    In column 2, line 13:  delete "zoom" and substitute
-- room -- therefor.
```

Signed and Sealed this

Seventh Day of April, 1998

Attest:

BRUCE LEHMAN

*Attesting Officer*        *Commissioner of Patents and Trademarks*